United States Patent [19]

Rivier et al.

[11] Patent Number: 4,661,472

[45] Date of Patent: Apr. 28, 1987

[54] GNRH ANTAGONISTS IX

[75] Inventors: Jean E. F. Rivier, La Jolla; Janos I. Varga, San Diego; Arnold T. Hagler, San Diego; R. Scott Struthers, San Diego; Marilyn H. Perrin, La Jolla; Catherine L. Rivier, La Jolla; Wylie W. Vale, Jr., La Jolla, all of Calif.

[73] Assignee: The Salk Institute for Biological Studies, San Diego, Calif.

[21] Appl. No.: 732,531

[22] Filed: May 9, 1985

[51] Int. Cl.$^4$ .................. A61K 37/43; C07K 7/06
[52] U.S. Cl. .................................. 514/15; 530/328
[58] Field of Search ............... 260/112.5 R; 514/15; 530/328

[56]  References Cited

U.S. PATENT DOCUMENTS

| 4,133,805 | 1/1979 | Yardley | 260/112.5 S |
| 4,140,767 | 2/1979 | Veber | 260/112.5 S |
| 4,482,486 | 11/1984 | Brtnik et al. | 260/112.5 R |
| 4,492,651 | 1/1985 | Sarantakis | 260/112.5 S |

OTHER PUBLICATIONS

GnRh Analogs: Structure—Activity Relationships, Jean Rivier et al., pp. 13-23, 1981.
Design of Peptide Analogs, Struthers and Hagler, pp. 239-261, 1984, American Chemical Society.

Primary Examiner—Delbert R. Phillips
Attorney, Agent, or Firm—Fitch, Even, Tabin & Flannery

[57]  ABSTRACT

Peptides which inhibit the secretion of gonadotropins by the pituitary gland and inhibit the release of steroids by the gonads. Administration of an effective amount of such GnRH antagonists prevents ovulation of female mammalian eggs and/or the release of steroids by the gonads. These peptides may be used to treat steroid-dependent tumors, such as prostatic and mammary tumors. The peptides are cyclic analogs of the decapeptide GnRH wherein there is a covalent bond between the residue in the 4-position and the residue in the 10-position. Examples of such bonds include the disulfide linkage between Cys residues, an amide linkage between a side chain amino group and a side chain carboxyl group, a dicarba linkage between side-chain alkyl groups, and a carba linkage between a side-chain alkyl group and a side-chain sulfhydryl group.

24 Claims, No Drawings

GNRH ANTAGONISTS IX

This invention was made with Government support under Grant No. HD-13527 and Contracts Nos. NO-1-HD-2-2807 and NO-1-HD-4-2833 awarded by the National Institutes of Health. The Government has certain rights in this invention.

The present invention relates to peptides which inhibit the release of gonadotropins by the pituitary gland in mammalians, including humans, and to methods of preventing ovulation and/or inhibiting the release of steroids. More particularly, the present invention is directed to peptides which inhibit gonadal function and the release of the steroidal hormones, progesterone and testosterone.

BACKGROUND OF THE INVENTION

The pituitary gland is attached by a stalk to the region in the base of the brain known as the hypothalamus. In particular, follicle stimulating hormone (FSH) and luteinizing hormone (LH), sometimes referred to as gonadotropins or gonadotropic hormones, are released by the pituitary gland. These hormones, in combination, regulate the functioning of the gonads to produce testosterone in the testes and progesterone and estrogen in the ovaries, and they also regulate the production and maturation of gametes.

The release of a hormone by the anterior lobe of the pituitary gland usually requires a prior release of another class of hormones produced by the hypothalamus. One of the hypothalamic hormones acts as a factor that triggers the release of the gonadotropic hormones, particularly LH, and this hormone is referred to herein as GnRH although it has also been referred to as LH-RH and as LRF. GnRH has been isolated and characterized as a decapeptide having the following structure:

p-Glu-His-Trp-Ser-Tyr-Gly-Leu-Arg-Pro-Gly-NH$_2$

Peptides are compounds which contain two or more amino acids in which the carboxyl group of one acid is linked to the amino group of the other acid. The formula for GnRH, as represented above, is in accordance with conventional representation of peptides where the amino terminus appears to the left and the carboxyl terminus to the right. The position of the amino acid residue is identified by numbering the amino acid residues from left to right. In the case of GnRH, the hydroxyl portion of the carboxyl group of glycine has been replaced with an amino group(NH$_2$). The abbreviations for the individual amino acid residues above are conventional and are based on the trivial name of the amino acid, e.g. pGlu is pyroglutamic acid, Glu is glutamic acid, His is histidine, Trp is tryptophan, Ser is serine, Tyr is tyrosine, Gly is glycine, Leu is leucine, Nle is norleucine, Orn is ornithine, Arg is arginine, Pro is proline, Sar is sarcosine, Phe is phenylalanine, Ala is alanine, Val is valine, Nva is norvaline, Ile is isoleucine, Thr is threonine, Lys is lysine, Asp is aspartic acid, Asn is asparagine, Gln is glutamine, Cys is cysteine, and Met is methionine. Except for glycine, amino acids of the peptides of the invention are of the L-configuration unless noted otherwise; however, the lower case abbreviation, i.e. asp, is used to designate either the L-or D-isomer, i.e. either Asp or D-Asp.

There are reasons for desiring to prevent ovulation in female mammalians, and the administration of GnRH analogs that are antagonistic to the normal function of GnRH have been used to suppress or delay ovulation. For this reason, analogs of GnRH which are antagonistic to GnRH are being investigated for their potential use as a contraceptive or for regulating conception periods. GnRH antagonists may also be used for the treatment of precocious puberty and endometriosis. Such antagonists have also been found useful to regulate the secretion of gonadotropins in male mammals and can be employed to arrest spermatogenesis, e.g. as male contraceptives, and for treatment of prostatic hypertrophy. More specifically, GnRH antagonists can be used to treat steroid-dependent tumors, such as prostatic and mammary tumors.

It is desired to provide improved peptides which are strongly antagonistic to endogenous GnRH and which prevent secretion of LH and the release of steroids by the gonads of mammals, and to provide compounds which are more effective in vivo when administered orally.

SUMMARY OF THE INVENTION

The present invention provides peptides which inhibit the release of gonadotropins in mammalians, including humans, and it also provides methods for inhibiting the release of steroids by the gonads of male and female mammalians. The improved GnRH analogs are strongly antagonistic to GnRH and have an inhibitory effect on the reproduction processes of mammalians; thus, they are referred to as GnRH antagonists. These analogs may be used to inhibit the production of gonadotropins and sex hormones under various circumstances, including precocious puberty, hormone dependent neoplasia, dysmenorrhea, endometriosis and steroid-dependent tumors.

Generally, in accordance with the present invention, peptides have been synthesized which strongly inhibit the secretion of gonadotropins by the pituitary gland of mammalians, including humans, and/or inhibit the release of steroids by the gonads. These peptides are cyclic analogs of GnRH wherein there is a covalent bond between the 4-position residue and the 10-position residue. These peptides should have a 1-position substitution, preferably dehydro-Pro or β-(1-or 2-naphthyl)-D-alanine(hereinafter β-D-1NAL or β-D-2NAL), a 2-position substitution in the form of a modified D-Phe and a 3-position substitution, preferably in the form of substituted D-Trp, D-3PAL or β-D-NAL. The 4-position substitution may be Cys, a diamino acid having not more than 5 carbon atoms, a dicarboxyl amino acid, such as Asp or Glu, or aBu. The 5-position may be occupied by (a) Tyr, (b) a halogenated or methylated Phe or Tyr, (c) His or preferably (d) Arg. The peptide has a 6-position substitution, an optional substitution in the 7-position, such as Nle, NML, Phe, Nva, Met, Tyr, Trp or PAL, optional substitutions in the 8- and 9-positions and a substitution in the 10-position that is complementary to the 4-position residue and that may be either the L- or D-isomer.

Modified D-Phe in the 2-position provides increased antagonistic activity as a result of the specific modifications present in the benzene ring. Single substitutions for hydrogen in the ring are preferably made in the para- or 4-position, but might be in either the 2- or 3-position also; the substitutions are selected from chloro, fluoro, bromo, methyl, methoxy and nitro, with chloro, fluoro and nitro being preferred. Dichloro substitutions are in the 2,4 or 3,4 positions in the ring. The alpha-carbon atom may also be methylated, e.g. (C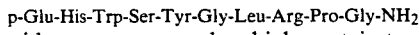

Me/4Cl)Phe. The 1-position substituent is preferably modified so that its alpha amino group contains an acyl group, such as formyl(For), acetyl(Ac), acrylyl(Acr), vinylacetyl(Vac) or benzoyl(Bz), with acetyl and acrylyl being preferred. PAL and D-PAL represent the L- and D-isomers of pyridyl-alanine where the β-carbon of Ala is linked to the 2-, 3- or 4-position, preferably to the 3-position, on the pyridine ring. When β-D-NAL is present in the 1-position and $R_5$ is not Arg, a hydrophilic D-amino acid residue, such as 4-$NH_2$-D-Phe, 4-guanido-D-Phe, D-His, D-Lys, D-Orn, D-Arg, D-Har(-Homoarginine) or D-PAL is preferably present in the 6-position. When dehydro-Pro is present in the 1-position, a D-isomer of a lipophilic amino acid, such as D-Trp, D-Phe, For-D-Trp, $NO_2$-D-Trp, D-Leu, D-Ile, D-Nle, D-Tyr, D-Val, D-Ala, D-Ser(OtBu), β-D-NAL or (imBzl)D-His is preferably in the 6-position, but D-PAL may be used.

These GnRH antagonists are very potent when administered orally. The peptides inhibit ovulation of female mammals when administered at low levels at proestrus and are also effective to cause resorption of fertilized eggs if administered shortly after conception. These peptides are also effective for the contraceptive treatment of male mammals and the treatment of steroiddependent tumors.

DETAILED DESCRIPTION OF THE PREFERRED EMBODIMENTS

More specifically, the peptides of the present invention are represented by the following Formula I:

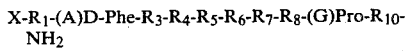

wherein X is hydrogen or an acyl group having 7 or less carbon atoms; $R_1$ is dehydro-Pro, D-pGlu, (A)D-Phe, (B)D-Trp, Pro, or β-D-NAL; A is H, Cl, F, $NO_2$, $CH_3$, $OCH_3$, $C^{\alpha}$Me/4Cl, $Cl_2$ or Br; B is H, $NO_2$, $NH_2$, $OCH_3$, F, Cl, Br, $CH_3$, $N^{in}$For or $N^{in}$Ac; $R_3$ is D-PAL, β-D-NAL or (B)D-Trp; $R_4$ is Cys, Asp, Glu, Orn, daB, daP or aBu; $R_5$ is Tyr, (C)Arg, (A)Phe, (3I)Tyr or His; $R_6$ is β-D-NAL, (B)D-Trp, (A')D-Phe, (D)D-Lys, (D)D-Orn, D-Har, D-Tyr, (E)D-His, D-PAL or (C)D-Arg; A' is A, $NH_2$, $NHCH_3$ or gua; C is (lower alkyl)$_n$ where n is 0, 1 or 2; D is X or an aryl group; E is H, imBzl or dinitrophenyl; $R_7$ is Nle, Leu, NML, Phe, Met, Nva, Tyr, Trp or PAL; $R_8$ is Arg, Ser, Tyr, Thr or PAL; G is H, OH or dehydro and $R_{10}$ is cys, asp, glu, orn, dab, dap or abu. When $R_1$ is β-D-NAL and $R_5$ is not Arg, then $R_6$ is preferably 4-$NH_2$-D-Phe, D-Lys, D-Orn, D-Har, D-His, 4-gua-D-Phe, D-PAL or D-Arg.

By dehydroPro is meant 3,4 dehydroproline, $C_5H_7O_2N$. By β-D-NAL is meant the D-isomer of alanine which is substituted by naphthyl on the β-carbon atom, i.e., also 3-D-NAL. Preferably β-D-2NAL is employed, the attachment to naphthalene is at the 2-position on the ring structure; however, β-D-1NAL may also be used. PAL represents alanine which is substituted by pyridyl on the β-carbon atom; preferably the linkage is to the 3-position on the pyridine ring. When substituted D-Trp is employed, single substitutions for hydrogen may be made in either the 5- or 6-position, which are selected from chloro, fluoro, bromo, methyl, amino, methoxy and nitro, with chloro, fluoro and nitro being preferred. Alternatively, the indole nitrogen may be acylated, e.g. with formyl ($N^{in}$-For- or 1For-) or with acetyl. $N^{in}$For-D-Trp and 6$NO_2$-D-Trp are the preferred substituted residues. By NML is meant $N^{\alpha}CH_3$-L-Leu. By aBu is meant a-amino butyric acid and by daB is meant a, γdiamino butyric acid. By daP is meant a,β diamino proprionic acid. When dehydro Pro is present in the 1-position, Tyr is preferably present in the 5-position and a lipophilic residue is in the 6-position. By 4-gua-D-Phe is meant a residue of D-Phe having guanidine substituted in the para-position. The guanido group of an Arg residue in the 5- or 6-position may be substituted once or twice by lower alkyl, i.e. 1 to 4 carbon atoms, e.g. propyl(Pr). When D-Lys or D-Orn is present in the 6-position, its side-chain-amino group may be substituted by acyl (1 to 7 carbon atoms) or by an aryl group having not more than 1 phenyl ring.

The peptides of the present invention can be synthesized by classical solution synthesis or by a solid phase technique using a chloromethylated resin, a hydroxymethylated resin, a methylbenzhydrylamine resin (MBHA), a benzhydrylamine (BHA) resin or any other suitable resin known in the art. The solid phase synthesis is conducted in a manner to stepwise add the amino acids in the chain in the manner set forth in detail in the U.S. Pat. No. 4,211,693. Side-chain protecting groups, as are well known in the art, are preferably added to the residues to be employed in the synthesis having particularly labile side chains and may optionally be added to others, such as Trp, before these amino acids are coupled to the chain being built upon the resin. Such synthesis provides the fully protected intermediate peptidoresin.

Chemical intermediates made generally in accordance with the invention may be represented by Formula II: $X^1$-$R_1$-(A)D-Phe-$R_3$($X^2$)-$R_4$($X^3$)-$R_5$($X^4$ or $X^5$)-$R_6$($X^4$ or $X^5$ or $X^6$)-$R_7$($X^2$ or $X^7$)-$R_8$'($X^4$ or $X^5$ or $X^8$)-(G)Pro-$R_{10}$($X^3$)-$X^9$ wherein: $X^1$ is an a-amino protecting group of the type known to be useful in the art in the stepwise synthesis of polypeptides and when X in the desired peptide composition is a particular acyl group, that group may be used as the protecting group. Among the classes of a-amino protecting groups covered by $X^1$ are (1) acyl-type protecting groups, such as formyl(-For), trifluoroacetyl, phthalyl, p-toluenesulfonyl(Tos), benzoyl(Bz), benzenesulfonyl, o-nitrophenylsulfenyl(Nps), tritylsulfenyl, o-nitrophenoxyacetyl, acrylyl(Acr), chloroacetyl, acetyl(Ac) and γ-chlorobutyryl; (2) aromatic urethantype protecting groups, e.g., benzyloxycarbonyl(Z), fluorenylmethyloxycarbonyl(-Fmoc) and substituted benzyloxycarbonyl, such as p-chlorobenzyloxycarbonyl(ClZ), p-nitrobenzyloxycarbonyl, p-bromobenzyloxycarbonyl and p-methoxybenzyloxycarbonyl; (3) aliphatic urethan protecting groups, such as tertbutyloxycarbonyl(Boc), diisopropylmethoxycarbonyl, isopropyloxycarbonyl, ethoxycarbonyl and allyloxycarbonyl; (4) cycloalkyl urethantype protecting groups, such as cyclopentyloxycarbonyl, adamantyloxycarbonyl and cyclohexyloxycarbonyl; (5) thiourethan-type protecting groups, such as phenylthiocarbonyl; (6) alkyl-type protecting groups, such as allyl(Aly), triphenylmethyl(trityl) and benzyl(Bzl); (7) trialkylsilane groups, such as trimethylsilane. The preferred a-amino protecting group is Boc when X is hydrogen.

$X^2$ is hydrogen or a protecting group for the indole nitrogen of Trp, such as Bz, Ac or For. In many syntheses there is no need to protect Trp, and such protection is not used if acylated D-Trp is present elsewhere in the peptide.

$X^3$ is a protecting group for the sulfhydryl group of Cys, preferably p-methoxybenzyl(MeOBzl), p-methylbenzyl, acetamidomethyl, trityl or Bzl; or a suitable protecting group for an amino side chain, e.g. Z,Cl-Z or t-amyloxycarbonyl; or a suitable, preferably hydrazine-labile, protecting group for a carboxyl side chain, such as OBzl(benzyl ester); or is a direct bond where the cyclic form results from a carba or dicarba bond.

$X^4$ is hydrogen or a protecting group for the phenolic hydroxyl group of Tyr selected from the group consisting of tetrahydropyranyl, tert-butyl, trityl, benzyl, Z, 4-bromobenzyloxycarbonyl and 2,6-dichlorobenzyl. 2,6-dichlorobenzyl(DCB) is preferred.

$X^5$ is a protecting group for a side chain guanido group, such as that in Arg, or for the imidazole group of His, such as nitro, Tos, trityl, adamantyloxycarbonyl, Z and 2,4-dinitrophenyl(DNP), or $X^5$ may be hydrogen, which means there is no protection on the side chain group atoms. Tos is generally preferred.

$X^6$ is a protecting group for an amino side chain group which is not removed when $X^3$ is removed from an amino side chain group in the 4- or 10-position which will thereafter take part in the cyclization, and is preferably Fmoc.

$X^7$ is hydrogen or a protecting group for Met, such as oxygen.

$X^8$ is a protecting group for a hydroxyl side chain of Ser or Thr, e.g. Ac, Bz, trityl, Bzl or DCB.

$X^9$ may be O—$CH_2$—[resin support], —NH—[resin support], OH, ester or $NH_2$.

The criterion for selecting side chain protecting groups for $X^2$-$X^8$ is that the protecting group should be stable to the reagent under the reaction conditions selected for removing the a-amino protecting group (preferably Boc) at each step of the synthesis. The protecting group should not be split off under coupling conditions but should be removable upon completion of the synthesis of the desired amino acid sequence under reaction conditions that will not alter the peptide chain. The protecting groups $X^3$ in some syntheses should be removable prior to the removal of the protecting group $X^6$.

When the $X^9$ group is —O—$CH_2$—[resin support], the ester moiety of one of the many functional groups of a polystyrene resin support is being represented. When the $X^9$ group is —NH—[resin support], an amide bond connects $R_{10}$ to a BHA resin or to a MBHA resin.

When X is acetyl, for example, in the final formula, it may be possible to employ it as the $X^1$ protecting group for the a-amino group of D-NAL or whatever amino acid is used in the 1-position by adding it before the coupling of this last amino acid to the peptide chain. However, a reaction is preferably carried out with the peptide on the resin (after deblocking the a-amino group while the side-chain groups remain protected), e.g. by reacting with acetic acid in the presence of dicyclohexyl carbodiimide (DCC) or preferably with acetic anhydride or by another suitable reaction as known in the art.

Cyclization is preferably effected of the linear peptide, as opposed to cyclizing the peptide while a part of the peptidoresin. When cyclization is effected via a disulfide linkage, the fully protected peptide can be cleaved from a hydroxymethylated resin or a chloromethylated resin support by ammonolysis, as is well known in the art, to yield the fully protected amide intermediate, which is thereafter suitably cyclized and deprotected; alternatively, deprotection as well as cleavage of the peptide from a benzhydrylamine resin, can take place at 0° C. with hydrofluoric acid (HF). Using some protocols, cyclization may be carried out while the partially protected peptide remains attached to the resin; however, it may not result in as good yields.

The cyclizing step for the GnRH peptide analog depends, of course, upon the type of linkage which is desired between the residues in the 4- and 10-positions. When residues of D- or L-Cys are included in both the 4- and 10-positions, it is convenient to carry out the cyclizing step following the cleavage from the resin and the removal of all of the protecting groups from the peptide. The cyclic form of the peptide is obtained by oxidizing using a ferricyanide solution, preferably as described in Rivier et al., *Biopolymers*, Vol. 17 (1978), 1927–38, or by air oxidation, or in accordance with other known procedures.

When the cyclization is via an amide bond between a side-chain amino group of the 4-position residue and a side-chain carboxyl group of the 10-position residue (which may be preferred), or vice-versa, it is preferable to synthesize the protected peptide on an MBHA or BHA resin and to derivatize the benzyl ester of the carboxyl acid side chain to the hydrazide while the peptide is still attached to the resin. This can be accomplished by using OBzl as a protecting group for the carboxyl side-chain of the residue to be involved in the amide-bond bridge and using Fmoc as a protecting group for any amino side chain on the 6-position residue. Following this selective hydrazide activation, deprotection of the remainder of the side-chain protecting groups except for any Fmoc protecting group upon a residue in the 6-position and cleavage from the resin are effected. Then reaction to accomplish cyclization is carried out by treating with isoamylnitrite and a strong acid, such as HCl, to generate the azide which in turn reacts with the free amino group, after a neutralization step, to generate the amide bond. Following cyclization, the peptide is completely deprotected by removal of any Fmoc group using a basic reagent, such as piperidine. In general, cyclizations of peptides in this overall fashion are exemplified by the teachings of the following U.S. Pat. Nos. 4,115,554, (Sept. 19, 1978); 4,133,805 (Jan. 9, 1979); 4,140,767 (Feb. 20, 1979); 4,161,521 (July 17, 1979); 4,191,754 (Mar. 4, 1980); 4,238,481 (Dec. 9, 1980); 4,244,947 (Jan. 13, 1981); and 4,261,885 (Apr. 14, 1981).

Analogs of GnRH including the equivalent of modified cysteine residues in the 4- and 10-positions wherein the disulfide linkage has been replaced by —$CH_2$— linkage are referred to as dicarba. If only one of the sulfhydryl groups is replaced by a $CH_2$-group, it is referred to as carba, e.g., [carba$^4$,Cys$^{10}$]—GnRH. Viewed from the aspect of the ultimate peptide, the location which would otherwise have been occupied by a Cys residue instead contains a residue of alpha-amino butyric acid(aBu). When preparing peptides having such a dicarba or carba-S linkage, the procedure set forth in U.S. Pat. No. 4,161,521 is preferably employed (the disclosure of which is incorporated herein by reference) so that, in the intermediate of Formula II, $X^3$ is a direct bond to the other residue.

Thus, the invention also provides a method for making a peptide or a nontoxic salt thereof, said peptide having the formula: X-$R_1$-(A)D-Phe-$R_3$-$R_4R_4$-$R_6$-$R_7$-$R_8$-(G)Pro-$R_{10}$-$NH_2$ wherein X is hydrogen or an acyl group having 7 or less carbon atoms; $R_1$ is dehydro-Pro, D-pGlu, (A)D-Phe, (B)D-Trp, Pro, or β-D-NAL; A is H, Cl, F, NO$_2$, C$^a$Me/4Cl, Cl$_2$ or Br; B is H, NO$_2$, NH$_2$, OCH$_3$, F, Cl, Br, CH$_3$, N$^{im}$For or N$^{im}$Ac; R$_3$ is D-PAL, β-D-NAL or (B)D-Trp; R$_4$ is Cys, Asp, Glu, Orn, daB, daP or aBu; R$_5$ is Tyr, (C)Arg, (A)Phe, (3I)Tyr or His; R$_6$ is β-D-NAL, (B)D-Trp, (A')D-Phe, (D)D-Lys, (D)D-Orn, D-Har, D-Tyr, (E)D-His, D-PAL or (C)D-Arg; A' is A, NH$_2$, NHCH$_3$ or gua; C is (lower alkyl)$_n$ where n is 0, 1 or 2; D is X or an aryl group; E is H, imBzl or dinitrophenyl; R$_7$ is Nle, Leu, NML, Phe, Met, Nva, Tyr, Trp or PAL; R$_8$ is Arg, Ser, Tyr, Thr or PAL; G is H, OH or dehydro and R$_{10}$ is cys, asp, glu, orn, dab, dap or abu; which method comprises (a) forming an intermediate compound having the formula:

X$^1$-R$_1$-(A)D-Phe-R$_3$(X$^2$)-R$_4$ (X$^3$)-R$_5$ (X$^4$ or X$^5$)-R$_6$(X$^4$ or X$^5$ or X$^6$)-R$_7$ (X$^2$ or X$^7$)-R$_8$ (X$^4$ or X$^5$ or X$^8$)-(G)Pro-R$_{10}$ (X$^3$)-X$^9$ wherein X$^1$ is hydrogen or an a-amino protecting group; X$^2$ is hydrogen or a protecting group for an indole nitrogen; X$^3$ is a direct bond, hydrogen or a protecting group for Cys or for a side-chain amino or carboxyl group; X$^4$ is hydrogen or a protecting group for a phenolic hydroxyl group of Tyr; X$^5$ is either hydrogen or a protecting group for a guanido or imidazole side chain; X$^6$ is a protecting group for an amino side chain; X$^7$ is a protecting group for Met; X$^8$ is a protecting group for an alcoholic hydroxyl group of Ser or Tyr; and X$^9$ is selected from the group consisting of O—CH$_2$—(resin support), —NH—(resin support), esters, and amides; (b) splitting off one or more of the groups X$^1$ to X$^8$ and/or cleaving from any resin support included in X$^9$; (c) optionally creating a cyclizing bond between R$_4$ and R$_{10}$ if not already present and, if desired, (d) converting a resulting peptide into a nontoxic salt thereof.

Purification of the peptide is effected by ion exchange chromatography on a CMC column, followed by partition chromatography using the elution system: n-butanol; 0.1N acetic acid (1:1 volume ratio) on a column packed with Sephadex G-25, or by using HPLC, as known in the art and specifically set forth in J. Rivier, et al. *J. Chromatography*, 288 (1984) 303–328.

The peptides of the invention are effective at levels of less than 100 micrograms per kilogram of body weight, when administered at about noon on the day of proestrus, to prevent ovulation in female rats. For prolonged suppression of ovulation, it may be necessary to use dosage levels in the range of from about 0.4 to about 2.5 milligrams per kilogram of body weight. These anatogonists are also effective to arrest spermatogenesis whe administered to male mammals on a regular basis and can thus be used as contraceptives. Since these compounds will reduce testosterone levels (an undesired consequence int henormal, sexually active male), it may be reasonable to administer replacement dosages of testosterone along with the GnRH antagonist. These anatagonists can also be used to regulate the production of gonadotropins and sec steroids for other purposes as indicated hereinbefore.

EXAMPLE I

Peptides as indicated in TABLE 1 having the formula:

Ac—R$_1$—(4Cl)D-Phe—D-3PAL—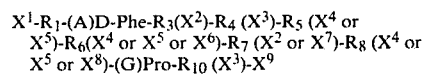

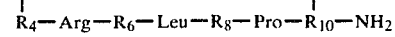

are prepared by the solid-phase procedure referred tO above.

TABLE I

| | R$_1$ | R$_4$ | R$_6$ | R$_8$ | R$_{10}$ |
|---|---|---|---|---|---|
| 1 | β-D-2NAL | Cys | D-3PAL | Arg | Cys |
| 2 | " | daP | " | " | Asp |
| 3 | dehydro Pro | Cys | β-D-2NAL | " | Cys |
| 4 | β-D-2NAL | " | D-Tyr | Thr | " |
| 5 | " | daP | D-3PAL | Arg | D-Asp |
| 6 | " | Orn | " | " | Asp |
| 7 | " | Asp | D-Tyr | Ser | daP |
| 8 | " | " | " | 3PAL | daP |
| 9 | " | Glu | " | 4PAL | " |
| 10 | " | " | D-2PAL | Tyr | daP |
| 11 | " | daB | (4gua)D-Phe | " | Asp |
| 12 | " | " | D-His | Ser | " |
| 13 | dehydro Pro | " | D-Leu | Arg | Glu |
| 14 | D-Trp | " | D-Phe | 4PAL | " |
| 15 | D-pGlu | daP | D-Ile | Thr | " |
| 16 | D-Phe | " | D-Val | 2PAL | Asp |

For purposes of an example, a representative solid phase synthesis of Peptide No. 1 above, which is referred to as [Ac-β-D-2NAL$^1$, (4Cl)D-Phe$^2$, D-3PAL$^{3,6}$, Cys$^{4,10}$,Arg$^5$]-GnRH is set forth hereinafter. This peptide has the following formula: Ac-β-D-2NAL-(4Cl)D-Phe-D-3PAL-Cys-Arg-D-3PAL-Leu-Arg-Pro-Cys-NH$_2$. The other peptides are similarly synthesized and purified.

A BHA resin is used, and Boc-protected Gly is coupled to the resin over a 2-hour period in CH$_2$Cl$_2$ using a 3-fold excess of Boc derivative and DCC as an activating reagent. The glycine residue attaches to the BHA residue by an amide bond.

Following the coupling of each amino acid residue, washing, deblocking and coupling of the next amino acid residue is carried out in accordance with the following schedule using an automated machine and beginning with about 5 grams of resin:

| STEP | REAGENTS AND OPERATIONS | MIX TIMES MIN. |
|---|---|---|
| 1 | CH$_2$Cl$_2$ wash-80 ml. (2 times) | 3 |
| 2 | Methanol(MeOH) wash-30 ml. (2 times) | 3 |
| 3 | CH$_2$Cl$_2$ wash-80 ml. (3 times) | 3 |
| 4 | 50 percent TFA plus 5 percent 1,2-ethanedithiol in CH$_2$Cl$_2$-70 ml. (2 times) | 10 |
| 5 | Isopropyl alcohol + 1% ethanedithiol wash-80 ml. (2 times) | 3 |
| 6 | TEA 12.5 percent in CH$_2$Cl$_2$-70 ml. (2 times) | 5 |
| 7 | MeOH wash-40 ml. (2 times) | 2 |
| 8 | CH$_2$Cl$_2$ wash-80 ml. (3 times) | 3 |
| 9 | Boc-amino acid (10 mmoles) in 30 ml. of either DMF or CH$_2$Cl$_2$, depending upon the solubility of the particular protected amino acid, (1 time) plus DCC (10 mmoles) in CH$_2$Cl$_2$ | 30–300 |
| 10 | MeOH wash-40 ml. (2 times) | 3 |
| 11 | TEA 12.5 percent in CH$_2$Cl$_2$-70 ml. (1 time) | 3 |
| 12 | MeOH wash-30 ml. (2 times) | 3 |
| 13 | CH$_2$Cl$_2$ wash-80 ml. (2 times) | 3 |

After step 13, an aliquot may be taken for a ninhydrin test: if the test is negative, go back to step 1 for coupling of the next amino acid; if the test is positive or slightly positive, go back and repeat steps 9 through 13.

The above schedule is used for coupling of each of the amino acids of the peptide of the invention after the first amino acid has been attached. $N^a$Boc protection is used for each of the remaining amino acids throughout the synthesis. $N^a$Boc-β-D-2NAL is prepared by a method known in the art, e.g. as described in detail in U.S. Pat. No. 4,234,571, issued November 18, 1980. The side chain of Arg is protected with Tos. MeOBzl is used as a side chain protecting group for the sulfhydryl group of Cys. $N^a$Boc-β-D-2NAL is introduced as the final amino acid. Boc-Arg(Tos), which has low solubility in $CH_2Cl_2$, is coupled using a $DMF:CH_2Cl_2$ mixture.

After deblocking the a-amino group at the N-terminal using trifluoroacetic acid(TFA), acetylation is achieved using a large excess of acetic anhydride in dichloromethane. The cleavage of the peptide from the resin and complete deprotection of the side chains takes place very readily at 0° C. with HF. Anisole is added as a scavenger prior to HF treatment. After the removal of HF under vacuum, the resin is extracted with 50% acetic acid, and the washings are lyophilized to provide a crude peptide powder.

The peptide is then air-oxidized for about 24 hours at about 22° C. to create a disulfide linkage between the Cys residues in each molecules.

Purification of the peptide is then effected by ion exchange chromatography on CMC (Whatman CM 32, using a gradient of 0.05 to 0.3M $NH_4OAc$ in 50/50 methanol/water) followed by partition chromatography in a gel filtration column using the elution system: n-Butanol; 0.1N Acetic acid (1:1-volume ratio).

The peptide is judged to be homogeneous using thin layer chromatography and several different solvent systems, as well as by using reversed-phase high pressure liquid chromatography and an aqueous triethylammonium phosphate solution plus acetonitrile. Amino acid analysis of the resultant, purified peptide is consistent with the formula for the prepared structure, showing substantially integer-values for each amino acid in the chain. The optical rotation is measured on a photoelectric polarimeter as $[a]_D^{22} = -37.8° \pm 1(c=1, 50\%$ acetic acid).

A peptide, such as No. 2 which is cyclized via an amide bond between the side chains of the residues in the 4- and 10-positions, may be made following the general teachings of U.S. Pat. Nos. 4,133,805 or 4,161,521. As an example of a suitable procedure, the following intermediate is assembled on a MBHA resin: Ac-β-D-2NAL-(4Cl)D-Phe-D-3PAL-daP(Z)-Arg(Tos)-D-3PAL-Leu-Arg(Tos)-Pro-Asp(OBzl)-MBHA resin support. The deprotection and cyclization are carried out as follows.

4 g. of protected-peptidyl resin is suspended at room temperature in 40 ml of DMF, and 1 ml. of anhydrous hydrazine (30–40x excess) is added to it under continuous stirring. Nitrogen is bubbled through the reactive mixture, and continuous stirring is effected in a closed vial for 48 hours. The resin is filtered, washed with DMF, MeOH, $CH_2Cl_2$ and MeOH, and finally dried.

4 g. of the protected peptide-hydrazide-resin is treated with 10–15 ml of distilled HF, in the presence of 1.5 ml of anisole as a scavenger, at 0° C. for 60 minutes to remove the remaining protecting groups and cleave the peptide from the resin. HF is removed under high vacuum, and the peptide is precipitated with anhydrous ethyl ether. The solid is collected, dissolved in 50 ml $CH_3CN:H_2O$ (1:1) and lyophilized. It is then purified using RP-HPLC, as described with respect to Peptide No. 1, prior to cyclizing.

1000 mg of the peptide-hydrazide is dissolved in 15 ml of DMF, cooled to −25° C., and bubbled through with $N_2$ gas. 0.56 ml (about 2.25 mmol) of 4N HCl in dioxane is added, and finally 105 μl (about 0.78 mmol) of isoamylnitrite is added over ten minutes. Stirring at −25° C. is continued for 3 hours. The azide-solution is diluted with 1000 ml of precooled DMF (−25° C.); N,N diisopropylethylamine is added in suitable portions to give a final pH of 7.8. The pH is checked and readjusted several times.

The solution is stored at 4° C. for 3 days, then evaporated to dryness in high vacuum. The residue is triturated in the presence of ethyl ether. The solid is collected and dried in vacuum.

The peptides are assayed in vivo and may also be tested in vitro. If performed, in vitro testing is carried out using dissociated rat pituitary cells maintained in culture for 4 days prior to the assay. The levels of LH mediated in response to the application of peptides is assayed by specific radioimmunoassay for rat LH. Control dishes of cells only receive a measure which is 3 nanomolar in GnRH; experimental dishes receive a measure 3 nanomolar in GnRH plus a measure having either the present standard antagonist for comparison purposes i.e. [Ac-dehydro Pro[1], (4F)D-Phe[2], D-Trp[3,6]]-GnRH or the test peptide, in concentrations ranging from 0.01 to 10 nanomolar. The amount of LH secreted in the samples treated only with GnRH is compared with that secreted by the samples treated with the peptide plus GnRH. The ability of the test peptide to reduce the amount of LH released by 3 nanomolar GnRH is compared to that of the present standard peptide.

The in vivo testing determines effectiveness to prevent ovulation in female rats. In this test, a specified number of mature female Sprague-Dawley rats, e.g. five to ten, each having a body weight from 225 to 250 grams, is injected with a specified microgram dosage of peptide in either saline or bacteriostatic water at about noon on the day of proestrus. Proestrus is the afternoon of ovulation. A separate female rat group is used as a control to which the peptide is not administered. Each of the control female rats ovulates on the evening of proestrus; of the rats treated, the number of them which ovulate is recorded. Each of the peptides is considered to be significantly effective to prevent ovulation of female rats at a very low dosage, and each peptide is considered to be totally effective at a dose of about 500 micrograms.

All peptides listed in Table I are considered effective to block GnRH-induced LH secretion in vitro at some reasonable concentration. Many of these peptides are more potent in vivo than the present standard. All of the peptides are considered to be effective to prevent ovulation of female mammals at low dosages. For example, in vivo testing of Peptide No. 1 at a dosage of 10 micrograms shows that only 7 rats out of 10 ovulate. Similar testing of No. 2 shows that, at a dosage of 10 μg, 9 out of 10 rats ovulate and at 50 μg, 0 out of 10 rats ovulate, while testing of No. 5 shows that at 50 μg only 2 out of 9 rats ovulate.

Example II

Peptides as indicated in TABLE II having the formula:

Ac—dehydroPro—(A)D-Phe—R₃—R₄—
         |
R₁₀—NH₂
                    —R₅—D-Trp—Leu—Arg—Pro— are prepared by the solid-phase procedure referred to above.

TABLE II

|    | A       | R₃           | R₄   | R₅         | R₁₀    |
|----|---------|--------------|------|------------|--------|
| 17 | 4F      | D-Trp        | Cys  | Tyr        | Cys    |
| 18 | "       | "            | daP  | "          | Asp    |
| 19 | 4Cl     | (1For)D-Trp  | Orn  | (2F)Phe    | "      |
| 20 | "       | "            | daB  | Tyr        | Glu    |
| 21 | "       | "            | "    | (2NO₂)Phe  | Asp    |
| 22 | "       | (1Ac)D-Trp   | daP  | (2CH₃)Phe  | "      |
| 23 | 4Br     | "            | "    | Tyr        | D-Glu  |
| 24 | "       | "            | daB  | (2Br)Phe   | "      |
| 25 | H       | D-Trp        | "    | (2Cl)Phe   | Asp    |
| 26 | 4NO₂    | (5CH₃)D-Trp  | "    | (3CH₃)Phe  | "      |
| 27 | "       | (5F)D-Trp    | Asp  | Tyr        | D-daP  |
| 28 | 2,4Cl₂  | (5Cl)D-Trp   | "    | (3F)Phe    | D-daB  |
| 29 | "       | (6NO₂)D-Trp  | Glu  | (3Br)Phe   | "      |
| 30 | CᵅMe/4Cl| (5OCH₃)D-Trp | aBu  | (3I)Tyr    | D-Cys  |
| 31 | 3,4Cl₂  | (5NH₂)D-Trp  | Cys  | (3Cl)Phe   | D-aBu  |

In vitro and/or in vivo testing of the peptides specified in Table II shows that the peptides listed in Table II are considered effective to block GnRH-induced LH secretion in vitro at a reasonable concentration. Many of these peptides are more potent in vivo than the present standard. All of the peptides are considered to be effective to prevent ovulation of female mammals at low dosages.

Example III

Peptides as indicated in TABLE III having the formula:

X—β-D-2NAL—(4Cl)D-Phe—D-3PAL—R₄—R₅—R₆—NML—
                                                    |
Arg—Pro—R₁₀—NH₂ are prepared by the solid-phase procedure referred to above.

TABLE III

|    | X    | R₄   | R₅        | R₆            | R₁₀    |
|----|------|------|-----------|---------------|--------|
| 32 | Ac   | Cys  | Tyr       | D-Arg         | aBu    |
| 33 | Acr  | aBu  | Arg       | D-Tyr         | D-aBu  |
| 34 | For  | Asp  | (Et₂)Arg  | "             | daP    |
| 35 | Bz   | "    | "         | (Et)D-Arg     | D-daB  |
| 36 | Ac   | daP  | (Et)Arg   | D-Lys         | D-Asp  |
| 37 | Vac  | "    | (Me₂)Arg  | D-Har         | Glu    |
| 38 | Acr  | Orn  | Arg       | (4gua)D-Phe   | "      |
| 39 | Ac   | daB  | (Pr)Arg   | D-Orn         | D-Asp  |
| 40 | Acr  | Cys  | (Bu)Arg   | D-His         | Cys    |
| 41 | Ac   | Orn  | His       | (Bu)D-Arg     | Asp    |
| 42 | "    | daP  | (Pr₂)Arg  | (Bz)D-Orn     | "      |
| 43 | Vac  | "    | (His      | 4NH₂)D-Phe    | D-Glu  |
| 44 | Bz   | Glu  | (Me)Arg   | (Ac)D-Lys     | daP    |

Peptides such as Nos. 32 and 33 are synthesized by employing the general teaching of U.S. Pat. No. 4,161,521.

In vitro and/or in vivo testing of the peptides specified in Table III shows that the peptides listed in Table III are considered effective to block GnRH-induced LH secretion in vitro at a reasonable concentration. Many of these peptides are more potent in vivo than the present standard. All of the peptides are considered to be effective to prevent ovulation of female mammals at low dosages.

Example IV

Peptides as indicated in TABLE IV having the formula:

Ac—R₁—(4Cl)D-Phe—D-Trp—R₄—
                              |
R₁₀—NH₂
                    —Tyr—D-3PAL—R₇—Arg—(G)Pro— are prepared by the solid-phase procedure referred to above.

TABLE IV

|    | R₁         | R₄  | R₇       | G       | R₁₀    |
|----|------------|-----|----------|---------|--------|
| 45 | β-D-2NAL   | Asp | Nle      | H       | daP    |
| 46 | (1Ac)D-Trp | "   | Met      | OH      | "      |
| 47 | (6Br)D-Trp | "   | Tyr      | H       | D-daB  |
| 48 | (5F)D-Trp  | "   | Nle      | dehydro | "      |
| 49 | (6NO₂)D-Trp| "   | Met      | "       | daB    |
| 50 | (5Cl)D-Trp | "   | Tyr      | H       | D-dap  |
| 51 | (4Cl)D-Phe | "   | Phe      | "       | Orn    |
| 52 | (4F)D-Phe  | "   | 4F-D-Phe | "       | "      |
| 53 | (2,4Cl₂)D-Phe | Glu | NML   | OH      | D-Orn  |
| 54 | dehydro Pro| "   | Nle      | "       | daB    |
| 55 | β-D-2NAL   | "   | Trp      | H       | "      |
| 56 | (6OCH₃)D-Trp| "  | Leu      | "       | daP    |
| 57 | (5NH₂)D-Trp| "   | Nva      | "       | "      |
| 58 | (4NO₂)D-Phe| "   | NML      | "       | D-daP  |
| 59 | dehydro Pro| "   | Tyr      | OH      | "      |

All peptides listed in Table IV are considered effective to block GnRH-induced LH secretion in vitro at some reasonable concentration. Many of these peptides are more potent in vivo than the present standard.

All of the peptides are considered to be effective to prevent ovulation of female mammals at low dosages.

Example V

Peptides as indicated in TABLE V having the formula:

Ac—R₁—(4F)D-Phe—R₃—R₄—Tyr—R₆—Tyr—Arg—
                                                |
Pro—R₁₀—NH₂ are prepared by the solid-phase procedure referred to above.

TABLE V

|    | R₁          | R₃          | R₄  | R₆             | R₁₀    |
|----|-------------|-------------|-----|----------------|--------|
| 60 | β-D-2NAL    | (6NO₂)D-Trp | Cys | (Et₂)D-Arg     | Cys    |
| 61 | "           | "           | "   | (DNP)D-His     | aBu    |
| 62 | "           | D-Trp       | "   | (4gua)D-Phe    | Cys    |
| 63 | dehydro Pro | β-D-2NAL    | "   | (6NO₂)D-Trp    | "      |
| 64 | dehydro Pro | β-D-1NAL    | "   | D-Val          | aBu    |
| 65 | β-D-2NAL    | (1For)D-Trp | "   | (Pr)D-Arg      | "      |
| 66 | "           | "           | aBu | (5NH₂)D-Trp    | D-Cys  |
| 67 | dehydro Pro | D-Trp       | "   | D-Tyr          | aBu    |
| 68 | "           | D-2PAL      | Glu | D-Nle          | D-daB  |
| 69 | "           | (1Ac)D-Trp  | "   | (4F)D-Phe      | Orn    |
| 70 | Pro         | D-3PAL      | Asp | β-D-1NAL       | daB    |
| 71 | (1For)D-Trp | "           | "   | (4NHCH₃)D-Phe  | D-daP  |
| 72 | β-D-2NAL    | "           | Cys | (Ac)D-Orn      | Cys    |
| 73 | "           | "           | "   | (4NH₂)D-Phe    | D-aBu  |
| 74 | β-D-1NAL    | (6Br)D-Trp  | "   | (1For)D-Trp    | Cys    |
| 75 | (6CH₃)D-    | D-4PAL      | Asp | D-4PAL         | D-daB  |

TABLE V-continued

| R₁ | R₃ | R₄ | R₆ | R₁₀ |
|---|---|---|---|---|
| Trp | | | | |

In vitro and/or in vivo testing of the peptides specified in Table V shows that the peptides listed in Table V are considered effective to block GnRH-induced LH secretion in vitro at a reasonable concentration. Many of these peptides are more potent in vivo than the present standard. All of the peptides are considered to be effective to prevent ovulation of female mammals at low dosages.

Example VI

Peptides as indicated in TABLE VI having the formula:

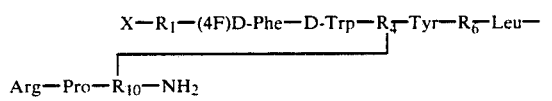

$$X-R_1-(4F)D-Phe-D-Trp-R_4-Tyr-R_6-Leu-Arg-Pro-R_{10}-NH_2$$

are prepared by the solid-phase procedure referred to above.

TABLE VI

| | X | R₁ | R₄ | R₆ | R₁₀ |
|---|---|---|---|---|---|
| 76 | Acr | dehydro-Pro | Asp | D-Val | D-daP |
| 77 | Ac | " | daP | β-D-2NAL | Asp |
| 78 | Ac | β-D-2NAL | Cys | D-Arg | Cys |
| 79 | Acr | Pro | Glu | D-Ser(OtBu) | D-Orn |
| 80 | H | dehydro-Pro | daP | (imBzl)D-His | Asp |
| 81 | Bz | (4Br)D-Phe | " | (5Cl)D-Trp | D-Glu |
| 82 | " | D-pGlu | " | (6Br)D-Trp | " |
| 83 | For | β-D-1NAL | " | (Me)D-Arg | D-Asp |
| 84 | " | dehydro-Pro | Cys | D-Har | aBu |
| 85 | Vac | β-D-2NAL | " | (Bz)D-Lys | D-Cys |
| 86 | " | D-Phe | daB | D-Ile | Asp |
| 87 | H | dehydro-Pro | " | D-Ala | Glu |

In vitro and/or in vivo testing of the peptides specified in Table VI shows that the peptides listed in Table VI are considered effective to block GnRH-induced LH secretion in vitro at a reasonable concentration. Many of these peptides are more potent in vivo than the present stadard. All of the peptides are considered to be effective to prevent ovulation of female mammals at low dosages.

Example VII

Peptides as indicated in TABLE VII having the formula:

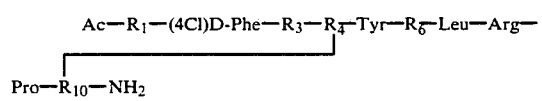

$$Ac-R_1-(4Cl)D-Phe-R_3-R_4-Tyr-R_6-Leu-Arg-Pro-R_{10}-NH_2$$

are prepared by the solid-phase procedure referred to above.

TABLE VII

| | R₁ | R₃ | R₄ | R₆ | R₁₀ |
|---|---|---|---|---|---|
| 88 | dehydro Pro | (6NO₂)D-Trp | Orn | β-D-2NAL | D-Glu |
| 89 | " | " | " | D-Val | Asp |
| 90 | " | (6F)D-Trp | daP | (4gua)D-Phe | " |
| 91 | " | " | " | (Bz)D-Orn | Glu |
| 92 | " | (5OCH₃)D-Trp | " | (For)D-Lys | " |
| 93 | " | " | " | D-2PAL | " |
| 94 | β-D-2NAL | (1Ac)D-Trp | Glu | D-Har | D-daP |
| 95 | " | (1For)D-Trp | " | (5CH₃)D-Trp | daB |
| 96 | dehydro Pro | (6Br)D-Trp | aBu | D-Nle | D-Cys |
| 97 | " | " | " | D-Leu | D-aBu |
| 98 | " | (6CH₃)D-Trp | " | β-D-2NAL | Cys |
| 99 | " | (6NH₂)D-Trp | Orn | (4NH₂)D-Phe | Glu |
| 100 | " | (5NH₂)D-Trp | " | (Acr)D-Lys | D-Asp |

In vitro and/or in vivo testing of the peptides specified in Table V shows that the peptides listed in Table V are considered effective to block GnRH-induced LH secretion in vitro at a reasonable concentration. Many of these peptides are more potent in vivo than the present standard. All of the peptides are considered to be effective to prevent ovulation of female mammals at low dosages.

Example VIII

Peptides as indicated in TABLE VIII having the formula:

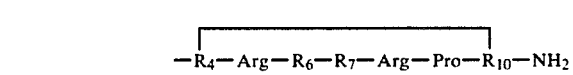

$$Ac-R_1-(4F)D-Phe-D-3PAL-R_4-Arg-R_6-R_7-Arg-Pro-R_{10}-NH_2$$

are prepared by the solid phase procedure referred to above.

TABLE VIII

| | R₁ | R₄ | R₆ | R₇ | R₁₀ |
|---|---|---|---|---|---|
| 101 | β-D-2NAL | Cys | (5NO₂)D-Trp | Leu | Cys |
| 102 | " | " | D-3PAL | " | aBu |
| 103 | " | aBu | β-D-2NAL | " | D-Cys |
| 104 | " | " | (Me₂)D-Arg | " | D-aBu |
| 105 | dehydroPro | " | β-D-2NAL | 3PAL | Cys |
| 106 | " | daP | (4NO₂)D-Phe | Tyr | Glu |
| 107 | β-D-2NAL | daB | D-3PAL | NML | " |
| 108 | " | daP | β-D-1NAL | 4PAL | D-Glu |
| 109 | " | Orn | (imBzl)D-His | Leu | " |
| 110 | " | Asp | (6NO₂)D-Trp | " | daP |
| 111 | " | Glu | D-Tyr | " | " |
| 112 | " | " | (1For)D-Trp | Phe | D-daP |
| 113 | " | " | (6F)D-Trp | NML | " |
| 114 | (CᵃMe/4Cl)D-Phe | " | (4Cl)D-Phe | Nle | D-Orn |
| 115 | Pro | Asp | (imBzl)D-His | Met | " |
| 116 | dehydroPro | " | (6OCH₃)D-Trp | Nva | daB |
| 117 | " | " | (5CH₃)D-Trp | " | D-daP |
| 118 | " | " | (1Ac)D-Trp | (4F)Phe | " |
| 119 | " | " | (Acr)D-Orn | NML | daP |
| 120 | " | Cys | (Et₂)D-Arg | Nle | aBu |
| 121 | " | " | β-D-2NAL | Trp | D-Cys |
| 122 | Pro | daP | (2,4Cl₂)D-Phe | Nva | Asp |
| 123 | β-D-2NAL | " | β-D-1NAL | Tyr | " |
| 124 | " | daB | (5Cl)D-Trp | Met | " |
| 125 | (4Cl)D-Phe | " | (4Br)D-Phe | 3PAL | Asp (acetate) salt |

The peptides described in TABLE VIII are tested in vivo to determine their effectiveness to prevent ovulation in female rats. All of them are considered to prevent ovulation of female rats at a low dosage, and to be totally effective at a dose of about 500 micrograms.

The peptides of the invention are often administered in the form of pharmaceutically acceptable, nontoxic salts, such as acid addition salts, or of metal complexes, e.g., with zinc, barium, calcium, magnesium, aluminum or the like (which are considered as addition salts for purposes of this application), or of combinations of the two. Illustrative of such acid addition salts are hydrochloride, hydrobromide, sulphate, phosphate, nitrate, oxalate, fumarate, gluconate, tannate, maleate, acetate, citrate, benzoate, succinate, alginate, malate, ascorbate, tartrate and the like. For example, an aqueous solution of the peptide can be repeatedly treated with 1N acetic acid and then lyophilized to yield the acetic acid salt thereof. If the active ingredient is to be administered in tablet form, the tablet may contain a pharmaceutically-acceptable diluent which includes a binder, such as tragacanth, corn starch or gelatin; a disintegrating agent, such as alginic acid; and a lubricant, such as magnesium stearate. If administration in liquid form is desired, sweetening and/or flavoring may be used as part of the pharmaceutically-acceptable diluent, and intravenous administration in isotonic saline, phosphate buffer solutions or the like may be effected.

The pharmaceutical compositions will usually contain the peptide in conjunction with a conventional, pharmaceutically-acceptable carrier. Usually, the dosage will be from about 10 micrograms to about 2.5 milligrams of the peptide per kilogram of the body weight of the host when given intravenously; although oral dosages will be higher, it is anticipated that the cyclic nature of these compounds will permit more effective oral administration. Overall, treatment of subjects with these peptides is generally carried out in the same manner as the clinical treatment using other antagonists of GnRH using a suitable carrier in which the peptide is soluble.

These peptides can be administered to mammals intravenously, subcutaneously, intramuscularly, orally, percutaneously, e.g. intranasally or intravaginally to achieve fertility inhibition and/or control and also in applications calling for reversible suppression of gonadal activity, such as for the management of precocious puberty or during radiation-or chemo-therapy. They are also useful for treatment of steroid-dependent tumors. Effective dosages will vary with the form of administration and the particular species of mammal being treated. An example of one typical dosage form is a bacteriostatic water solution containing the peptide which solution is administered to provide a dose in the range of about 0.1 to 2.5 mg/kg of body weight. Oral administration of the peptide may be given in either solid form or liquid form.

Although the invention has been described with regard to its preferred embodiments, it should be understood that changes and modifications as would be obvious to one having the ordinary skill in this art may be made without departing from the scope of the invention which is set forth in the claims which are appended hereto. For example, other substitutions known in the art which do not significantly detract from the effectiveness of the peptides may be employed in the peptides of the invention. D-2PAL and D-4PAL are considered to be equivalents of D-3PAL. Substituted Phe, such as (4F)Phe, can be used instead of Phe in the 7-position. Other hydrophobic amino acid residues can also be employed in the 1-position, preferably in D-isomer form, and are considered equivalents of those specified. Moreover, the amino side chain of D-Lys or D-Orn in the 6-position instead of being substituted with a acyl group may be substituted with a dipeptide or a tripeptide which are considered equivalents.

Particular features of the invention are emphasized in the claims which follow.

What is claimed is:

1. A peptide or a nontoxic salt thereof, said peptide having the formula: X-$R_1$-(A)D-Phe-$R_3$-$R_4$-$R_5$-$R_6$-$R_7$-$R_8$-(G)Pro-$R_{10}$-$NH_2$ wherein X is hydrogen or an acyl group having 7 or less carbon atoms; $R_1$ is dehydro-Pro, D-pGlu, (A)D-Phe, (B)D-Trp, Pro, or β-D-NAL; A is H,Cl, F, $NO_2$, $CH_3$, $OCH_3$, $C^aMe/4Cl$, $Cl_2$ or Br; B is H, $NO_2$, $NH_2$, $OCH_3$, F, Cl, Br, $CH_3$, $N^{in}$For or $N^{in}$Ac; $R_3$ is D-PAL, β-D-NAL or (B)D-Tro; $R_4$ is Cys, Asp, Glu, Orn, daB, daP or aBu; $R_5$ is Tyr, (C)Arg, (A)Phe, (3I)Tyr or His; $R_6$ is β-D-NAL, (B)D-Trp, (A')D-Phe, (D)D-Lys, (D)D-Orn, D-Har, D-Tyr, (E)D-His, D-PAL or (C)D-Arg; A' is A, $NH_2$, $NHCH_3$ or gua; C is (lower alkyl)$_n$ where n is 0, 1 or 2; D is X or an aryl group; E is H, imBzl or dinitrophenyl; $R_7$ is Nle, Leu, NML, Phe, Met, Nva, Tyr, Trp or PAL; $R_8$ is Arg, Ser, Tyr, Thr or PAL; G is H, OH or dehydro and $R_{10}$ is cys, asp, glu, orn, dab, dap or abu; provided however that when $R_4$ is Cys or aBu, $R_{10}$ is cys or abu; when $R_4$ is Asp or Glu, $R_{10}$ is orn, dab or dap; and When r4 is Orn, daB or daP, $R_{10}$ is asp or glu.

2. A peptide in accordance with claim 1 wherein A is 4Cl or 4F.

3. A peptide in accordance with claim 1 wherein $R_4$ is Asp or Glu and $R_{10}$ is orn, dab or dap.

4. A peptide in accordance with claim 1 wherein $R_4$ is Orn, daB or daP and $R_{10}$ is asp or glu.

5. A peptide in accordance with claim 1 wherein $R_4$ is Cys and $R_{10}$ is cys or abu.

6. A peptide in accordance with claim 1 wherein $R_3$ is (B)D-Trp and B is $6NO_2$ or $N^{in}$For.

7. A peptide in accordance with claim 1 wherein $R_1$ is β-D-2NAL, $R_3$ is D-PAL and $R_5$ is Arg.

8. A peptide in accordance with claim 7 wherein $R_6$ is D-Trp, D-PAL, β-D-NAL, (imBzl)D-His or ($6NO_2$)D-Trp.

9. A peptide in accordance with claim 7 wherein $R_6$ is (imBzl)D-His or ($6NO_2$)D-Trp and $R_7$ is Leu.

10. A peptide in accordance with claim 6 wherein $R_4$ is Cys or aBu and $R_{10}$ is cys.

11. A peptide in accordance with claim 1 wherein $R_4$ is aBu and $R_{10}$ is abu.

12. A peptide in accordance with claim 1 wherein $R_8$ is Arg and G is H.

13. A peptide in accordance with claim 12 wherein D and E are both H and n is O.

14. A peptide in accordance with claim 1 wherein X is Ac, A is 4Cl or 4F and G is H.

15. A peptide in accordance with claim 1 wherein $R_4$ is Asp, $R_8$ is Arg and $R_{10}$ is D-Orn.

16. A peptide in accordance with claim 1 wherein $R_3$ is (B)D-Trp, B is $6NO_2$ or $N^{in}$For and $R_8$ is Arg.

17. A peptide in accordance with claim 1 wherein $R_1$ is dehydroPro, $R_3$ is D-PAL, $R_5$ is Arg and $R_8$ is Arg.

18. A peptide in accordance with claim 1 wherein $R_4$ is Orn, $R_8$ is Arg and $R_{10}$ is D-Asp.

19. A peptide in accordance with claim 14 wherein $R_6$ is (imBzl)D-His or ($6NO_2$)D-Trp, $R_7$ is Leu, Nle, NML or PAL and $R_8$ is Arg.

20. A peptide in accordance with claim 1 wherein $R_4$ is daP and $R_{10}$ is Asp.

21. A peptide in accordance with claim 20 wherein $R_3$ is D-3Pal, $R_5$ is Arg and $R_6$ is D-3Pal.

22. A peptide in accordance with claim 21 wherein X is Ac and $R_1$ is D-2-Nal.

23. A peptide in accordance with claim 22 wherein A is 4Cl or 4F, $R_7$ is Leu, $R_8$ is Arg and G is H.

24. A method for regulating the secretion of gonadotropins comprising administering an effective amount of a peptide or a nontoxic salt thereof as defined in claim 1.

* * * * *

UNITED STATES PATENT AND TRADEMARK OFFICE
CERTIFICATE OF CORRECTION

PATENT NO. : 4,661,472
DATED : April 28, 1987
INVENTOR(S) : Jean E. F. Rivier, et al.

It is certified that error appears in the above-identified patent and that said Letters Patent is hereby corrected as shown below:

Column 3, lines 25-26, change "steroiddependent" to
--steroid-dependent--.

Column 6, line 66, change "$R_4R_4$" to --$R_4$-$R_5$--.

Column 7, line 49, change "0.4" to --0.1--,

Column 7, line 52, change "whe" to --when--,

Column 7, line 55, change "int henormal" to --in the normal--,

Column 7, line 59, change "sec" to --sex--.

Column 8, line 6, change "t0" to --to--,

Column 8, line 28, change "$Cys^{4\ 10}$" to --$Cys^{4,10}$--.

Column 12, line 25, change "D-dap" to --D-daP--.

Column 16, line 6, change "(B)D-Tro" to --(B)D-Trp--,

UNITED STATES PATENT AND TRADEMARK OFFICE
CERTIFICATE OF CORRECTION

PATENT NO. : 4,661,472
DATED : April 28, 1987
INVENTOR(S) : Jean E. F. Rivier, et al Page 2 of 2

It is certified that error appears in the above-identified patent and that said Letters Patent is hereby corrected as shown below:

Column 16, line 17, change "when r4" to -- when $R_4$ --.

Signed and Sealed this

Twenty-seventh Day of October, 1987

Attest:

DONALD J. QUIGG

Attesting Officer

Commissioner of Patents and Trademarks